United States Patent [19]

Muoio et al.

[11] Patent Number: 5,510,566
[45] Date of Patent: Apr. 23, 1996

[54] REGENERANT RECYCLE PROCESS FOR OXYGENATE REMOVAL

[76] Inventors: Vincent A. Muoio, 10 Concord La.; Richard Caruso, 53 Acadia Dr., both of Voorhees, N.J. 08043

[21] Appl. No.: 354,365

[22] Filed: Dec. 12, 1994

[51] Int. Cl.$^6$ .......................... C07C 7/12; C07C 41/00; C07C 43/00
[52] U.S. Cl. .................... 585/824; 585/800; 568/697; 568/699
[58] Field of Search .................... 585/800, 824; 568/697, 699

[56] References Cited

U.S. PATENT DOCUMENTS 4,447,653  5/1984  Vora ............................... 568/697

OTHER PUBLICATIONS

M. B. Rao and S. Sircar, Production of Motor Fuel Grade Alcohol by Concentration Swing Adsorption, 1992, pp. 1875–1887.
S. Sakata, H. Kuribayashi and I. Sugawara, Advanced Radwaste System, pp. 255–262.
F. Raiter, D. Glasser and A. W. Bryson, The regenneration of weak and strong cation exchange resions with an aqueous solution of $SO_2$, pp. 93–105.
E. Korngold, Water Desalination by Ion–Exchange Hollow Fibers, pp. 123–135.
J. P. van der Hoek and A. Klapwijk, Reduction of Regeneration Salt Requiremetn and Waste Disposal in an Ion exchange Process for Nitrate removal From Ground Water, 1989, pp. 203–210.
P. C. Chiang and J. E. Etzel, A New Regeneration Technique for Mixed–Bed Ion–Exchanger Process, 1986, pp. 307–317.
Robert Trubac, The $C_4$ Raffinate Treatment Process Methanol Recovery/Oxygenate Removal, 1987, pp. 1–18.

*Primary Examiner*—Sharon Gibson
*Attorney, Agent, or Firm*—Crockett & Fish

[57] ABSTRACT

In methyl tertiary butyl ether (MTBE) plant n-butane is used to regenerate a molecular sieve adsorption bed of an oxygen removal unit, and contaminated n-butane is purified by distillation and recycled for further regeneration. The requirement for n-butane is thus reduced and little or no contaminated n-butane need be diverted for use as fuel gas.

18 Claims, 1 Drawing Sheet ium-size">5,510,566

REGENERANT RECYCLE PROCESS FOR OXYGENATE REMOVAL

BACKGROUND OF THE INVENTION

The present invention relates to the field of oil refining, and more specifically to the field of MTBE production.

Methyl tertiary butyl ether (MTBE) is a commercially important compound useful as a gasoline blending octane component. Annual worldwide MTBE production is presently well over 14 million gallons per day.

MTBE may be commercially produced by processes well known in the art from isobutylene and methanol. Alternatively n-butene or butanes can be used in place of isobutylene, and typically a mixed $C_4$ feedstock is used. The raffinate from such processes have relatively small quantities of oxygenated compounds including by-product dimethyl ether, unreacted methanol and MTBE product and also have other contaminants such as sulfur compounds and butadiene. The oxygenates are typically separated out from $C_4$ raffinate in an oxygen removal unit.

Oxygen removal units of the molecular sieve adsorption type require regeneration after a period of use. Regeneration employs relatively large quantities of a regenerant such as n-butane, which can be problematic in that the amount of n-butane required may exceed that available in a typical refinery, and contamination of the n-butane during the regeneration process reduces its commercial value. In addition, contaminated n-butane, which in the past could be readily blended with gasoline, cannot be blended with gasoline in the quantities required because of new more restrictive vapor pressure regulations.

One solution presently in operation at several MTBE plants is to partially recycle the regenerant. This solution, however, is not completely satisfactory because the buildup of oxygenates and other contaminants prevents recycling of the same regenerant beyond a certain point. For example, MTBE plants which recycle n-butane regenerant still utilize at least approximately 33% of the amount of fresh n-butane which would be employed by similar plants using oncethrough regeneration. Further recycling of the spent regenerant has long been considered impractical because the regenerant typically has a vapor pressure which makes it difficult to separate out other components. For example, the order of pure component vapor pressures (highest to lowest) for the more important components are DME, 1,3 butadiene, n-butane, MTBE and methanol.

SUMMARY OF THE INVENTION

The present invention reduces the amount of fresh regenerant required to regenerate the molecular sieve in an oxygen removal unit of an MTBE plant by using n-butane as the regenerant, by recycling the n-butane, and by distilling out contaminants from the recycled n-butane. The invention relies upon the recognition that methanol is azeotropic with DME and miscellaneous $C_4$ contaminants, and can be readily separated from the n-butane and MTBE in a distillation tower.

Accordingly, it is an object of this invention to reduce the amount of fresh regenerant utilized in an oxygen removal unit of an MTBE plant.

BRIEF DESCRIPTION OF THE DRAWING

This and other objects of the present invention will become better understood through a consideration of the following description taken in conjunction with the drawing in which.

DETAILED DESCRIPTION OF THE PREFERRED EMBODIMENTS

Figure 1:
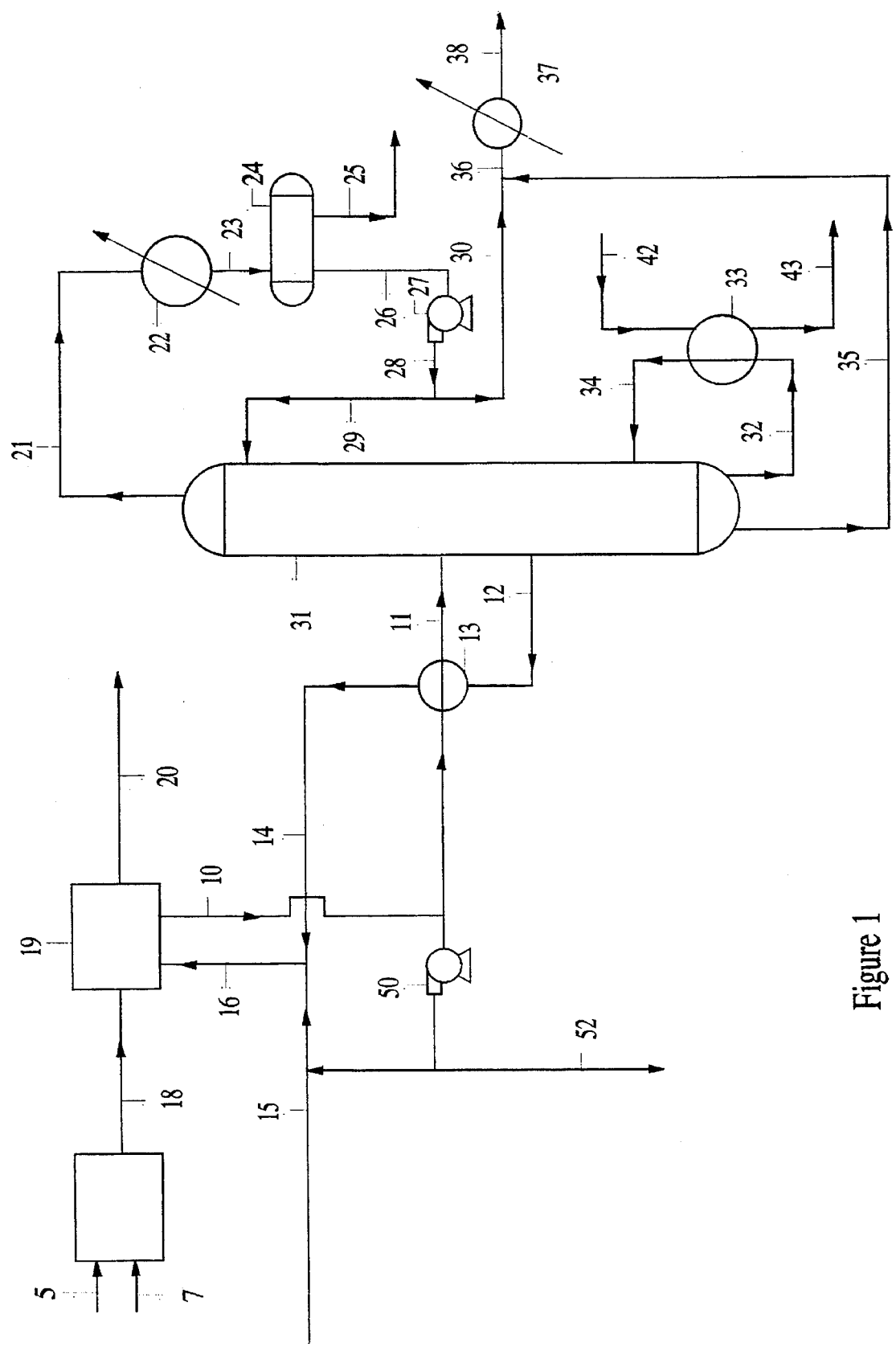
FIG. 1 is schematic of a preferred embodiment of an MTBE plant.

Turning now to the drawing, FIG. 1 schematically depicts a preferred embodiment of an MTBE plant according to the present invention.

Lines 5 and 7 carry $C_4$ and methanol streams respectively to an MTBE reaction unit 17 which may have single or multiple stages. The $C_4$ line 5 typically contains a mixed stream of butane and butylene. The m-ethanol Stream 7 typically contains relatively pure m-ethanol. Reaction unit 17 may produce MTBE according to known processes. See e.g., Hydrocarbon Processing, October 1984, pages 64–66. Depending on the precise characteristics of the precursors and the process used, the MTBE unit will produce some combination of MTBE and by-product DME. A small fraction of MTBE and most of the DME A are carried by line 18 to an oxygen removal unit 19. 1,3 butadiene, n-butane and some other non-reactants from line 5 pass through the MTBE unit unchanged. Unreacted and unrecovered methanol from line 7 also exits the MTBE unit. These components are also carried by line 18 to an oxygen removal unit 19.

The oxygen removal unit 19 utilizes a molecular sieve adsorption process to separate out oxygenates, including MTBE. This leaves a stream of deoxygenated mixed $C_4$ raffinate which passes through line 20 to make alkylate in a hydrofluoric acid (HF) alkylation unit (not shown), or for some other purpose.

Over time the molecular sieve in the oxygen removal unit 19 requires regeneration, and n-butane is preferably used for this purpose. Uncontaminated or marginally contaminated n-butane enters the oxygen removal unit 19 through line 16, and contaminated n-butane, having been used to regenerate the molecular sieve beds, exits through line 10. Some of the contaminated n-butane can be passed by pump 50 and line 52 to be used a fuel gas, but most of the contaminated n-butane is advantageously passed through heat exchanger 13, and fed through line 11 to a distillation tower 31. In the distillation tower 31, methanol distills azeotropically with DME and miscellaneous $C_4$ components, and is primarily carried overhead in line 21. Regenerated, relatively pure n-butane exits distillation tower 31 in line 12, and the remaining components including MTBE leave the distillation tower 31 as a bottoms product stream in line 35.

The specific characteristics and operation of distillation tower 31 are well within the ordinary skill of the art. When the cooling water temperature is 88° F., and the tower 31 is advantageously operated, the pressure at top of the tower is 121 psig and the top temperature varies through the cycle between 140° F. and 150° F. Heat is preferably added to the tower 31 through the recirculation of fluids through line 32, reboiler 33, and line 34. Reboiler 33 is heated by steam passing through lines 42 and 43.

The distillate stream carried by line 21 is preferably passed to condenser 22 and then through line 23 to overhead receiver 24. Water is removed from the receiver 24 through line 25, and condensed methanol, DME and miscellaneous $C_4$ components are pumped by pump 27 through lines 26 and 28 either back into the distillation tower 31 via line 29, or out of the system via line 30. The distillate stream carried by line 30 may leave the system as a separate stream, or may be combined with the bottoms stream carried by line 35. In a preferred embodiment, and as shown in FIG. 1, the two streams are combined into line 36, pass through heat exchanger 37, and exit along with spent n-butane regenerant via line 38. If these streams are kept separate the result is two distinct streams, the bottoms stream having essentially all the MTBE, and the distillate stream having essentially all the methanol and DME.

The regenerated n-butane exiting the distillation tower 31 in line 12 passes through heat exchanger 13 and can be used once again to regenerate the molecular sieve bed of the oxygen removal unit 19. Since some n-butane is lost either in the distillation tower 31 or is used as fuel gas, fresh make-up regenerant is added through line 15. In a preferred embodiment, however, none of the regenerant feed goes to the fuel gas system and about 2.5 percent exits with the spent regenerate. This is to about 33 percent in previous systems.

The favorable economics of the present invention is based in large measure upon the difference in value of contaminated butane from the oxygen removal unit being used as fuel gas, and the same contaminated butane being regenerated and reused, and/or sent to the gasoline pool. In an exemplary reference period, the Fall of 1992, the value of both butane and gasoline (before taxes) was approximately $0.10/lb, and the value of fuel gas was only $0.06/lb:

Butane—$0.485/gal÷4.87 lb/gal=$0.10/lb

Gasoline—$0.618/gal÷6.26 lb/gal=$0.10/lb Fuel Gas—$2.75/10^6 Btu*21,133 Btu/lb=$0.06/lb.

In a plant utilizing previously available technology and having a capacity of 1,414 barrels per day of MTBE, about 15,700 lb/hr of fresh butane is used to regenerate the molecular adsorption sieve bed of the oxygen removal unit. The cost of the fresh butane is about $12,560,000/yr (15,700 lb/hr*8,000 hr/yr*$0.10/lb).

After including by-products such as DME, MeOH, 1–3 Butadiene and unrecoverable MTBE, the quantity of contaminated butane products to be disposed of is 15,923 lb/hr. Most refineries could not blend nearly this quantity of these components in gasoline, and a large measure would be diverted to fuel gas as follows:

Butane to gasoline: 1,423 lb/hr

Butane to fuel gas: 14,500 lb/hr The value of the butane blended into gasoline would be about $1,138,000/yr (1,423 lb/hr*8000 hr/yr*$0.10/lb), and the value of the butane burned as fuel gas would be about $6,960,000/yr (14,500 lb/hr*8000 hr/yr*$0.06/lb). Thus, the total cost of the butane would be about $4,462,000/yr ($12,560,000–$1,138,000–$6,960,000).

A system according to the present invention would only require fresh butane feed of about 1,200 lb/hr, and essentially all of the butane not used for regeneration of the molecular sieve bed would be blended into gasoline. In such a system the cost of the fresh butane would be about $960,000/yr (1,200 lb/hr * 8,000 hr/yr*$0.10/lb), and the value of the butane blended into gasoline would be about $1,138,000/yr (1,423 lb/hr*8000 hr/yr*$0.10/lb). The net effect would therefore be an increase in the value of butane of about $178,000/yr as opposed to a net cost for butane of about $4,462,000/yr. This equates to an overall net gain of about $4,640,000/yr.

Again using the Fall of 1992 as a reference, it was calculated that an embodiment of the present invention would have saved approximately $5.1 million per year in butane and gasoline value, compared with a capital cost of implementation of only $1.54 million. The actual savings and costs would, of course, vary depending upon the circumstances at each refinery, but are expected to be comparable.

Thus, a regenerant recycle process and apparatus for use in MTBE production has been disclosed. While specific embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:

1. A process for recycling regenerant contaminated with oxygenates during regeneration of an oxygen removal unit of an MTBE plant, comprising:

providing said regenerant consisting essentially of n-butane in a regenerant stream independent of any MTBE process stream;

directing said regenerant to a distilling unit;

distilling said regenerant in said distilling unit to remove at least some of said oxygenates; and returning at least some of said regenerant to said oxygen removal unit.

2. The process of claim 1 wherein said distilling unit comprises a distilling tower, said oxygenates primarily leave said tower as an overhead stream, purified regenerant leaves said tower as a mid-tower stream, and said MTBE leaves said tower as a bottom stream.

3. The process of claim 1 wherein at least 80% by weight of said distilled regenerant is recycled to said oxygen removal unit.

4. The process of claim 1 wherein at least 90% by weight of said distilled regenerant is recycled to said oxygen removal unit.

5. An MTBE plant comprising:

a feed stream;

an MTBE process unit which converts at least part of the feed stream into MTBE, $C_4$ raffinate and oxygenates;

an oxygen removal unit containing a molecular adsorption sieve for separating said raffinate from said oxygenates;

an n-butane regenerant stream which is substantially independent of the feed stream, and contains a regenerant which becomes contaminated with said oxygenates in regenerating said adsorption sieve; and a distilling apparatus whereby said oxygenates are separated from said contaminated regenerant to produce substantially decontaminated regenerant.

6. The MTBE plant of claim 5 wherein at least 80% by weight of said decontaminated regenerant is recycled to said oxygen removal unit.

7. The MTBE plant of claim 5 wherein at least 90% by weight of said decontaminated regenerant is recycled to said oxygen removal unit.

8. The MTBE plant of claim 5 wherein said distilling unit comprises a distilling tower, said oxygenates primarily leave said tower as an overhead stream, purified regenerant leaves said tower as a mid-tower stream, and said MTBE leaves said tower as a bottom stream.

9. An improved MTBE plant producing $C_4$ raffinate and oxygenates as by-products, said plant having an oxygen removal unit containing a molecular adsorption sieve for separating said raffinate from said oxygenates, and a regenerant used primarily to regenerate the molecular sieve and thereby becoming contaminated with said oxygenates said improvement comprising:

said regenerant consisting essentially of n-butane;

a distilling apparatus whereby said oxygenates are separated from said contaminated regenerant; and at least 80% by weight of said decontaminated regenerant is recycled to said oxygen removal unit.

10. The MTBE plant of claim 11 wherein at least 90% by weight of said decontaminated regenerant is recycled to said oxygen removal unit.

11. An MTBE plant comprising:

an oxygen removal unit containing a molecular adsorption sieve;

an n-butane regenerant for regenerating said molecular adsorption sieve;

means for decontaminating and recycling said regenerant whereby usage of fresh said regenerant is reduced by at least 80% by weight over usage of said regenerant which is non-recycled.

12. The MTBE plant of claim 11 wherein comprises predominantly n-butane and n-butane and said means comprises a distilling tower which separates n-butane from contaminants added to said n-butane during said regeneration.

13. The MTBE plant of claim 12 wherein usage of fresh said regenerant is reduced by at least 90% over usage of said regenerant which is non-recycled.

14. The MTBE plant of claim 12 wherein usage of fresh said regenerant is reduced by at least 95% over usage of said regenerant which is non-recycled.

15. The MTBE plant of claim 11 wherein said oxygenates compromise light and heavy oxygenates.

16. The MTBE plant of claim 11 wherein methanol and MTBE are removed from the regenerant before recycling said regenerant for reuse.

17. The MTBE plant of claim 2 wherein methanol is removed from the distilling tower as an overhead stream.

18. The MTBE plant of claim 5 wherein methanol is removed from the distilling apparatus tower as an overhead stream.

* * * * *